(12) United States Patent
Schweikard et al.

(10) Patent No.: US 7,318,805 B2
(45) Date of Patent: *Jan. 15, 2008

(54) APPARATUS AND METHOD FOR COMPENSATING FOR RESPIRATORY AND PATIENT MOTION DURING TREATMENT

(75) Inventors: Achim Schweikard, Hamburg (DE); John R. Adler, Stanford, CA (US)

(73) Assignee: Accuray Incorporated, Sunnyvale, CA (US)

( * ) Notice: Subject to any disclaimer, the term of this patent is extended or adjusted under 35 U.S.C. 154(b) by 567 days.

This patent is subject to a terminal disclaimer.

(21) Appl. No.: 10/273,598

(22) Filed: Oct. 18, 2002

(65) Prior Publication Data

US 2003/0125622 A1    Jul. 3, 2003

Related U.S. Application Data

(63) Continuation of application No. 09/657,771, filed on Sep. 8, 2000, now Pat. No. 6,501,981, which is a continuation-in-part of application No. 09/270,404, filed on Mar. 16, 1999, now Pat. No. 6,144,875.

(51) Int. Cl.
*A61B 6/00* (2006.01)
*A61B 8/00* (2006.01)

(52) U.S. Cl. ..................... 600/439; 600/427
(58) Field of Classification Search ............. 600/424, 600/407, 425–429, 410–411, 413–417, 439, 600/471; 606/130; 378/69
See application file for complete search history.

(56) References Cited

U.S. PATENT DOCUMENTS 4,132,896 A    1/1979   Klotz et al.

(Continued)

FOREIGN PATENT DOCUMENTS

EP        1004272 A     5/2000

(Continued)

OTHER PUBLICATIONS

Minohara, S. et al., "Respiratory Gated Irradiation System for Heavy-Ion Radiotherapy", International Journal of Radiation: Oncology Biology Physics, Pergamon Press, US, vol. 47, No. 4, Jul. 1, 2000, ISSN: 0360-3016.

*Primary Examiner*—Francis J. Jaworski
(74) *Attorney, Agent, or Firm*—Blakely, Sokoloff, Taylor & Zafman LLP

(57) ABSTRACT

An apparatus and method for performing treatment on an internal target region while compensating for breathing and other motion of the patient is provided in which the apparatus comprises a first imaging device for periodically generating positional data about the internal target region and a second imaging device for continuously generating positional data about one or more external markers attached to the patient's body or any external sensor such as a device for measuring air flow. The apparatus further comprises a processor that receives the positional data about the internal target region and the external markers in order to generate a correspondence between the position of the internal target region and the external markers and a treatment device that directs the treatment towards the position of the target region of the patient based on the positional data of the external markers.

33 Claims, 16 Drawing Sheets

U.S. PATENT DOCUMENTS

| | | | |
|---|---|---|---|
| 4,237,901 A * | 12/1980 | Taenzer | 600/443 |
| 4,583,538 A | 4/1986 | Onik et al. | |
| 5,207,223 A * | 5/1993 | Adler | 600/427 |
| 5,222,499 A | 6/1993 | Allen et al. | |
| 5,394,875 A * | 3/1995 | Lewis et al. | 600/445 |
| 5,397,329 A | 3/1995 | Allen | |
| 5,411,026 A * | 5/1995 | Carol | 600/439 |
| 5,447,154 A * | 9/1995 | Cinquin et al. | 600/429 |
| 5,537,452 A | 7/1996 | Shepherd et al. | |
| 5,588,430 A | 12/1996 | Bova et al. | |
| 5,622,187 A | 4/1997 | Carol | |
| 5,628,315 A | 5/1997 | Vilsmeier et al. | |
| 5,727,554 A * | 3/1998 | Kalend et al. | 600/587 |
| 5,769,861 A | 6/1998 | Vilsmeier | |
| 5,784,431 A | 7/1998 | Kalend et al. | |
| 5,797,849 A | 8/1998 | Vesely et al. | |
| 5,967,981 A | 10/1999 | Watrous | |
| 5,971,997 A | 10/1999 | Guthrie et al. | |
| 6,006,126 A | 12/1999 | Cosman | |
| 6,076,005 A | 6/2000 | Sontag et al. | |
| 6,120,453 A | 9/2000 | Sharp | |
| 6,144,875 A | 11/2000 | Schweikard et al. | |
| 6,246,898 B1 * | 6/2001 | Vesely et al. | 600/424 |
| 6,307,914 B1 | 10/2001 | Kunieda et al. | |
| 6,314,312 B1 * | 11/2001 | Wessels et al. | 600/427 |
| 6,405,072 B1 * | 6/2002 | Cosman | 600/426 |
| 6,501,981 B1 * | 12/2002 | Schweikard et al. | 600/427 |

FOREIGN PATENT DOCUMENTS

| | | |
|---|---|---|
| JP | 62-206798 | 9/1987 |
| JP | 6-181918 | 7/1994 |
| JP | 11-19082 | 1/1999 |
| JP | 2000-201922 | 7/2000 |
| JP | 2000-217810 | 8/2000 |
| WO | WO 92/06644 | 4/1992 |
| WO | WO 00/07669 | 2/2000 |

* cited by examiner

SYSTEM BLOCK DIAGRAM

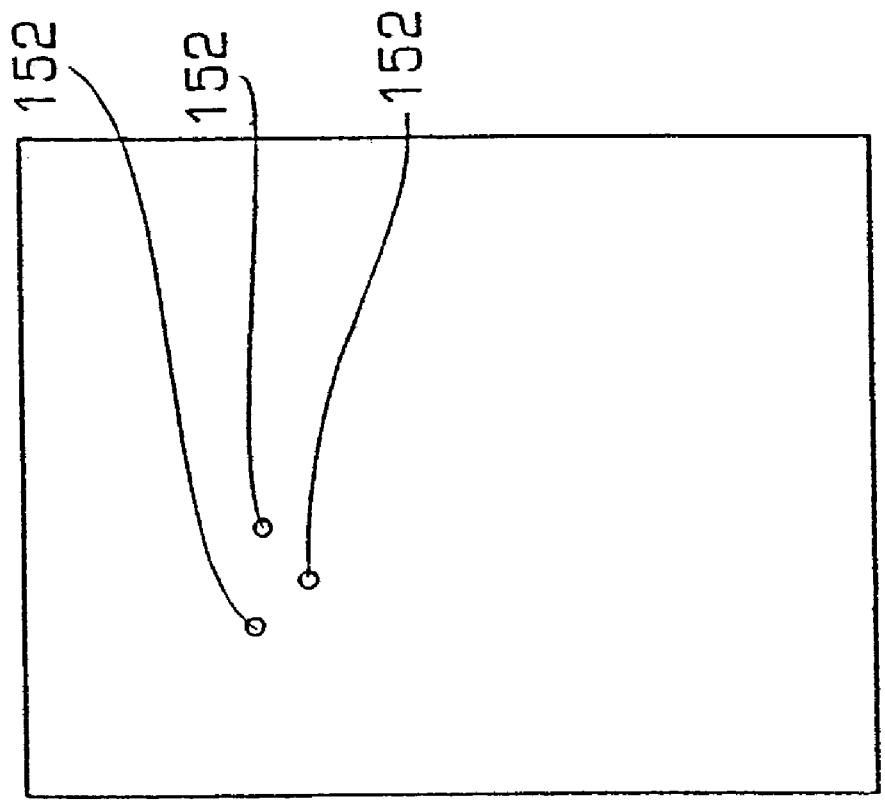
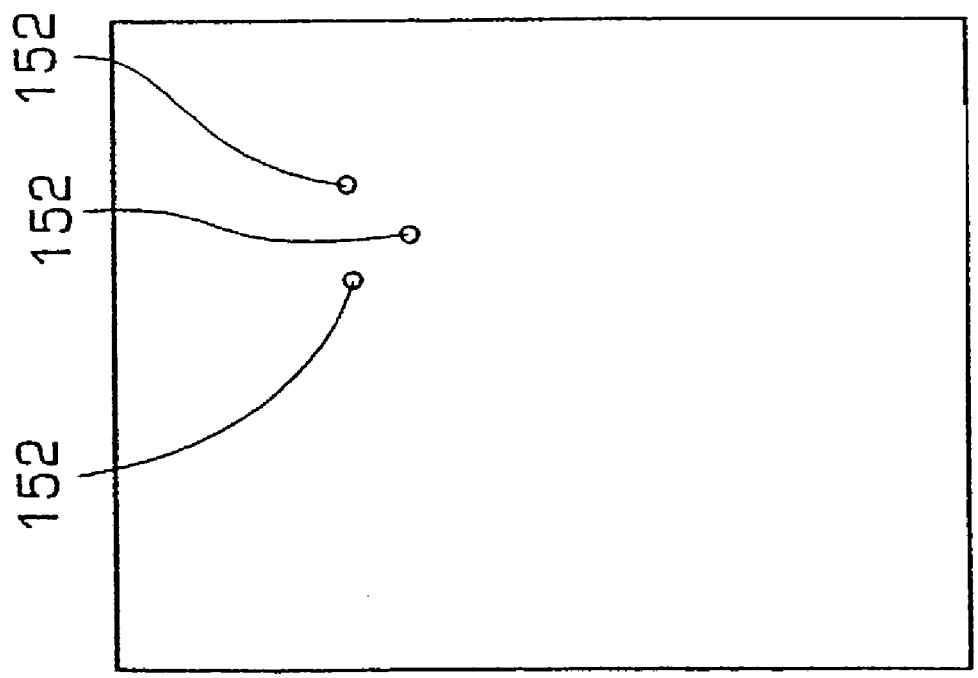

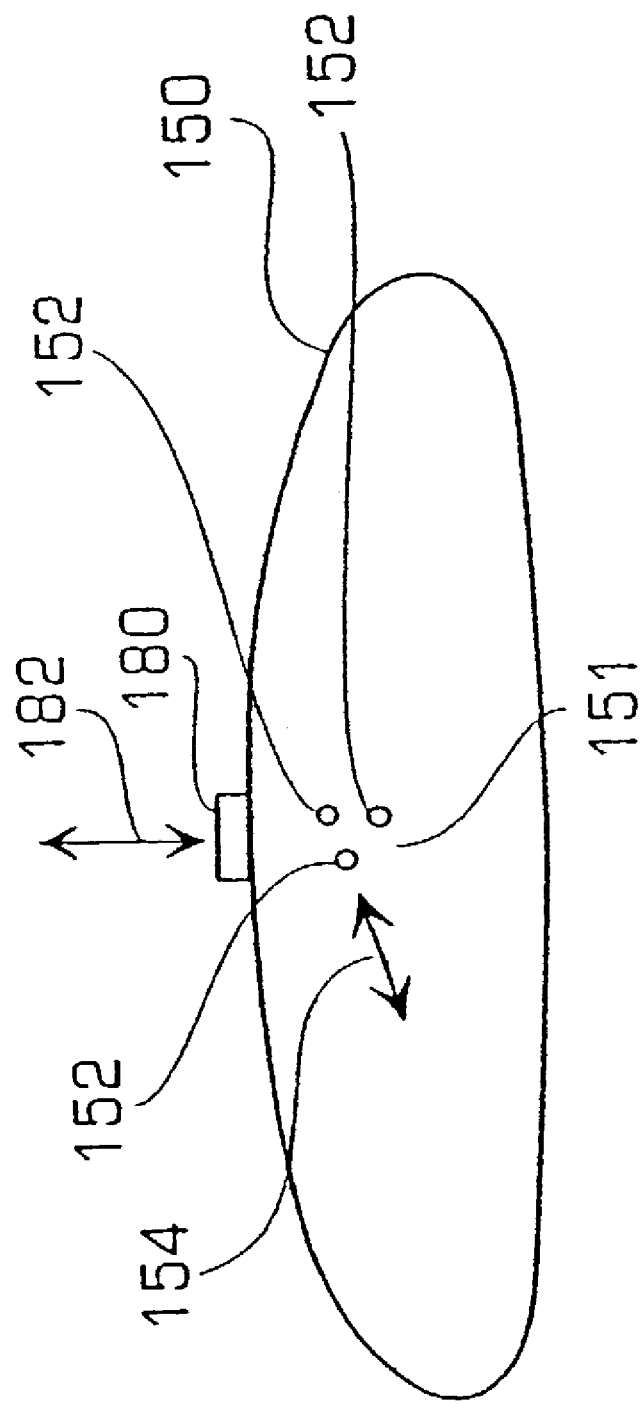

APPARATUS AND METHOD FOR COMPENSATING FOR RESPIRATORY AND PATIENT MOTION DURING TREATMENT

RELATED APPLICATION

This application is a continuation application of U.S. patent application Ser. No. 09/657,771 filed Sep. 8, 2000 now U.S. Pat. No. 6,501,981 which is in turn is a continuation-in-part application of U.S. patent application Ser. No. 09/270,404 now U.S. Pat. No. 6,144,875 filed on Mar. 16, 1999. Both of these applications are incorporated herein by reference.

BACKGROUND OF THE INVENTION

This invention relates generally to an apparatus for improving the accuracy and efficacy of surgical treatments and more particularly to locating a target region to be treated and tracking the motion of the target region due to respiratory and other patient motions during the treatment.

Various different treatments may accurately track the motion of a target region in order to apply the treatment to the target region. In radiation therapy and radiosurgery, for example, a tumor may be destroyed by a beam of ionizing radiation which kills the cells in the tumor. The problem is that the tumor may move during treatment, especially due to the breathing motion of the patient. Such respiratory motion is difficult to track using external sensors, since the extent and direction of the internal breathing motion of the patient cannot be seen with traditional imaging devices. The breathing and other motion of the patient means that it is more difficult to focus the radiation on the tumor which means that the treatment may be less effective and healthy tissue may be unnecessarily damaged.

The goal of radiosurgery is to give a very high dose of radiation to the tumor only, while protecting surrounding healthy tissue as much as possible. Although radiosurgery has been applied with dramatic success to brain tumors, the extension of this technique to tumors outside the head or neck areas has eluded easy solutions. The main reason for this difficulty has been the problem of accurate target localization (i.e., accurate tracking of the motion of the target). In particular, breathing motion and other organ and patient motion make it difficult to track the target tumor with high precision. Thus, in the presence of breathing motion, for example, it is difficult to achieve the goal of providing a high dose of radiation to the tumor while protecting surrounding healthy tissue. Therefore radiosurgery is currently applied nearly exclusively to brain tumors. Conventional systems can only move the radiation beam along circular arcs in space so that irregular breathing motions cannot be easily followed since these breathing motions may not occur along the axis of the circular arcs traced by the radiation beam.

Another radiosurgery technique uses a mechanical robotic device having six degrees of freedom that targets a radiation beam as disclosed in U.S. Pat. No. 5,207,223 to Adler. The robotic device permits the radiation treatment beam to be accurately positioned to apply the treatment beam directed to the target region. A method for neurosurgical navigation is disclosed in U.S. Pat. No. 5,769,861. This method relates to finding fixed targets, such as a brain tumor, but does not address tracking the motion of a target organ, such as lung due to breathing, with respect to the skin surface, or tracking the motion of internal abdominal organs with respect to externally visible motion. A fiducial that may be implanted into the human body so that it is detectable by an imaging system is also disclosed in which the fiducial implant is implanted into the bone or organs of the human body. This fiducial implant permits internal structures of the human body to be analyzed, but does not attempt to compensate for motion of a target organ which moves throughout the respiratory cycle. Thus, it is desirable to provide an apparatus and method for compensating for respiratory and other patient motion in radiation treatment and it is to this end that the present invention is directed.

SUMMARY OF THE DISCLOSURE

A method is described for compensating for motions of a patient during treatment. The method includes generating pre-operative three-dimensional images of an internal region showing an internal fiducial and a target region located in the internal region. The method also includes acquiring an ultrasound image of the internal region, the ultrasound image showing the internal fiducial. The method also includes matching the internal fiducial in the ultrasound image with the internal fiducial in one of the pre-operative three-dimensional images to determine a position of the target region.

An apparatus is described for compensating for a motion of a patient during treatment. The apparatus includes a beaming apparatus to generate a treatment beam, an ultrasound imaging device for periodically generating internal positional data about an internal target region, and a processor to receive the internal positional data and external positional data to generate a correlation between a position of the internal target region and an external marker. The processor is further configured to generate a control signal to move the beaming apparatus to direct the treatment beam toward the target region based on the external positional data.

Another method is described for compensating for motions of a patient during treatment. The method includes generating images of a target region prior to the treatment, periodically generating ultrasound images indicating positional data about the target region during the treatment, and moving a linear accelerator to direct a treatment beam at a position of the target region based on the ultrasound images.

The internal markers may be imaged using a number of different imaging technologies, including x-rays, nuclear magnetic resonance, ultrasound and other technologies which permit markers inside of the body of the patient to be imaged. Alternatively, three dimensional ultrasound images may be used to establish the location of the internal target region in lieu of discrete fiducials. The position of the external sensor may also be determined using a number of different technologies including infrared imaging, visual imaging, magnetic localization, the measurement of respiration, and any other type of technology which permits the external markers to be imaged. In addition to using external sensors (i.e., external fiducials may not be used), it is also possible to visually image a body surface which is then correlated to the internal fiducials.

Thus, in accordance with the invention, an apparatus for performing treatment on an internal target region while measuring and in some cases compensating for breathing and other motion of the patient is provided. The apparatus comprises a first imaging device for periodically generating positional data about the internal target region and a second imaging device for continuously generating positional data about one or more external markers attached to the patient's body. The apparatus further comprises a processor that receives the positional data about the internal target region and the external sensor readings/measurements in order to generate a correspondence between the position of the internal target region and the external marker or sensor readings and a treatment device that directs the treatment towards the position of the target region of the patient based on the positional data of the external markers or sensor readings. An apparatus for compensating for motion of a patent during treatment is also disclosed as well as a method for compensating for motion of the patient.

In accordance with another embodiment of the invention, no fiducials are attached to the target, the target is delineated in x-ray images (manally or semi-automatically), and the target's position is subsequently matched to the position of the tumor in preoperative tomographic images. In addition, motions of the target region resulting from pulsation effects can be compensated for via a sensor by recording both pulsation data and time points of pulsation data acquisition or both pulsation and respiratory motions may be compensated for simultaneously. In addition, the deformation or squeezing of the target region may be determined and that deformation may be compensated.

In accordance with yet another aspect of the invention, a single image of the patient may be used to generate a model and then the patient is instructed to return to the position within the respiration cycle corresponding to this single point. In addition, the motion model in accordance with the invention may be continuously updated. In addition,a general model for a particular motion may be determined. In addition, the time lag between a command and the beam actually being at that position may be compensated for. Finally, respiratory motion may be distinguished from other motion.

BRIEF DESCRIPTION OF THE DRAWINGS

FIGS. 7A-7D are diagrams illustrating the imaging of the internal markers in accordance with the invention;

FIG. 8 is a diagram illustrating the internal markers in combination with an external marker to track the motion of the target region in accordance with the invention;

DETAILED DESCRIPTION OF A PREFERRED EMBODIMENT

Figure 1:
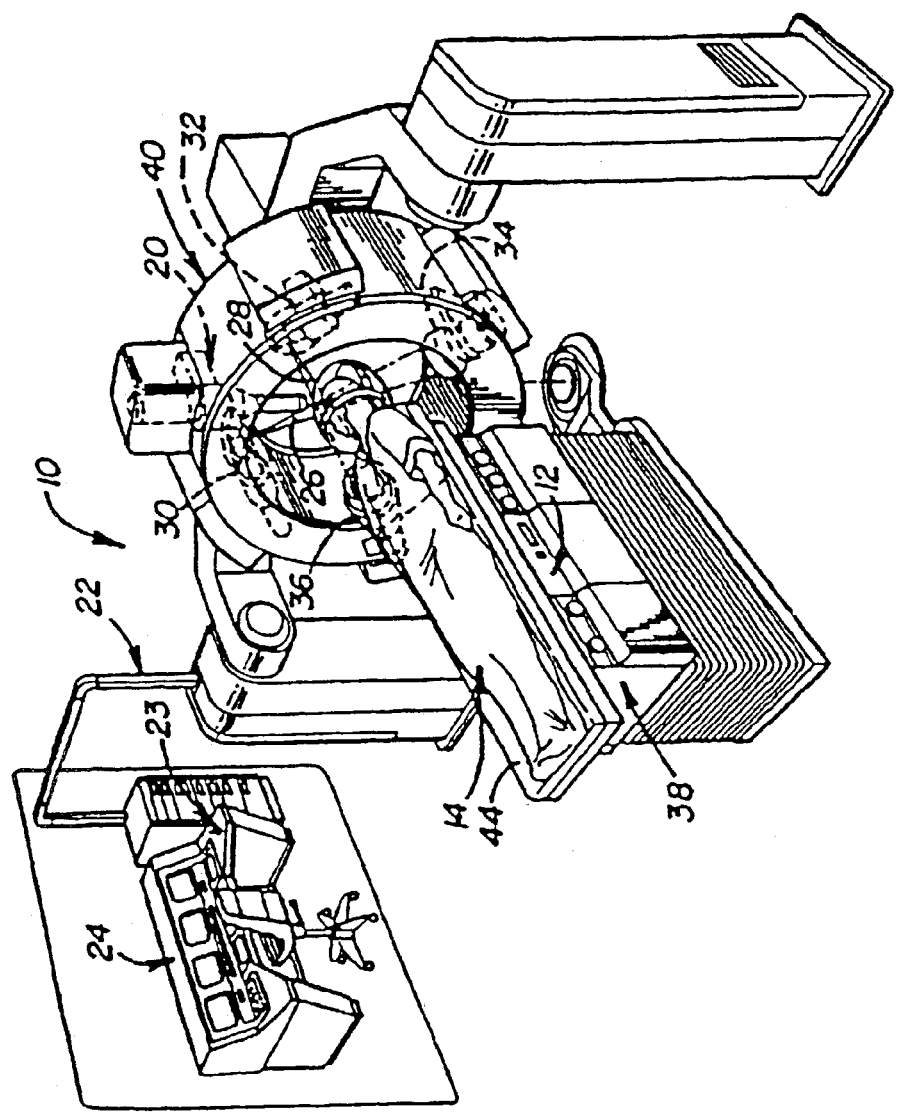
FIG. 1 is a diagram illustrating a conventional radiation treatment device.

The invention is particularly applicable to an apparatus and method for compensating for breathing and other patient motion during radiation treatment (radiosurgery) and it is in this context that the invention will be described. It will be appreciated, however, that the apparatus and method in accordance with the invention has greater utility, such as to other types of medical procedures with other types of medical instruments, such as positioning biopsy needles, ablative, ultrasound or other focused energy treatments, or positioning a laser beam for laser beam treatment. Prior to describing the invention, a typical radiosurgery device will be described to provide a better understanding of the invention.

FIGS. 1-4 are diagrams illustrating an example of a stereotaxic radiation treatment device 10. The radiation treatment device 10 may include a data processor 12, such as a microprocessor, and a disc or tape storage unit 13 (shown in FIG. 4) which may store a three dimensional image of a patient 14. The three dimensional image may be loaded into the data processor, if not already there, to compare the three dimensional image to images generated during the surgical procedure. The three dimensional image may be generated by various conventional techniques such as computer aided tomography (CAT) scan or magnetic resonance imaging (MR). The radiation treatment device 10 may also include a beaming apparatus 20 which, when activated, emits a collimated ionizing beam directed at a target region 18 (shown in FIG. 2). The collimated surgical ionizing beam may have sufficient strength to cause the target region to become necrotic. A variety of different beaming apparatus may be used which generate an ionizing radiation or heavy particle beam such as a linear accelerator, a synchrocyclotron or preferably an x-ray linear accelerator. Such an x-ray beaming apparatus is commercially available. The beaming apparatus may be activated by the operator throwing a switch 23 at a control console 24 connected to the beaming apparatus 20 by a cable 22.

Figure 2:
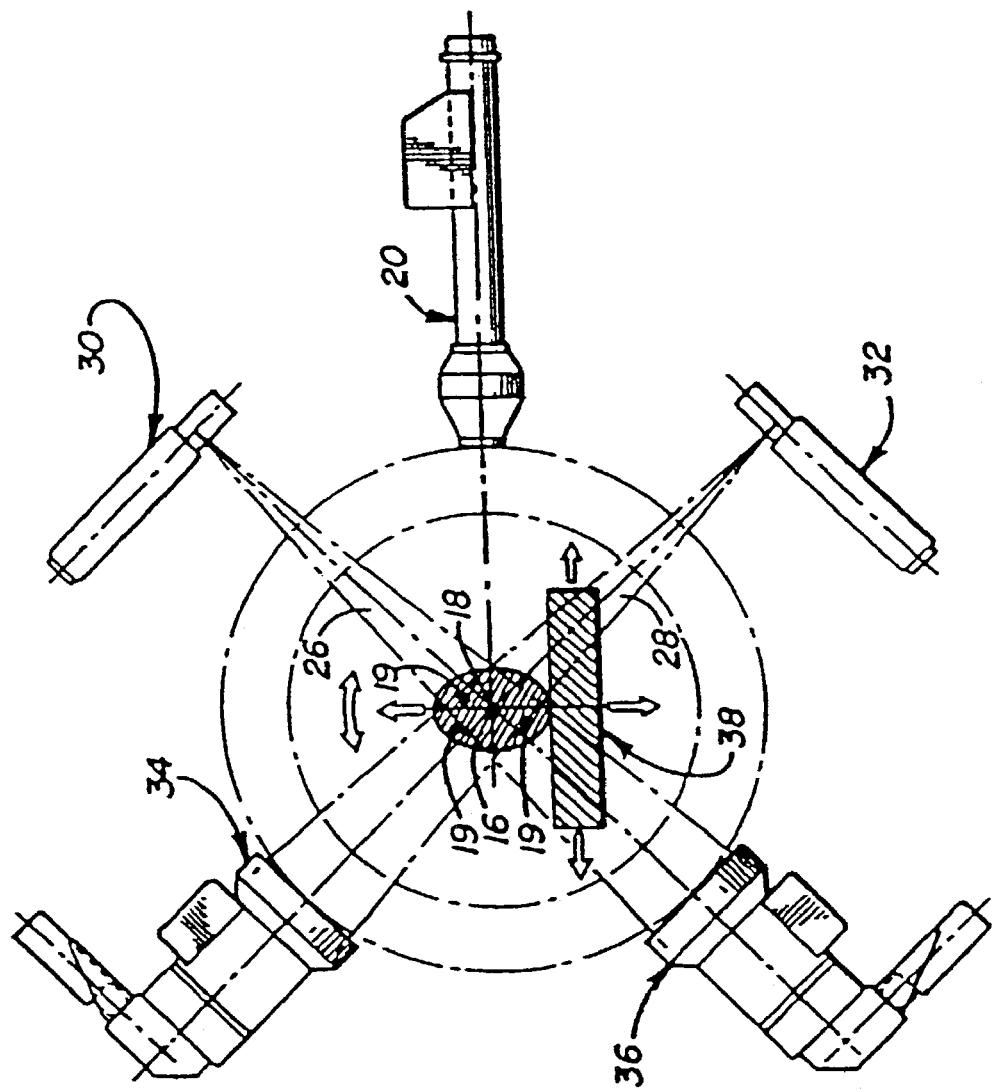
FIG. 2 is a diagram illustrating more details of the radiation treatment device.

The radiation treatment device 10 may also include an apparatus for passing a first diagnostic beam 26 and a second diagnostic beam 28 through the region previously imaged by the three-dimensional image. The diagnostic beams are positioned at a predetermined non-zero angle with respect to each other, such as being orthogonal as shown in FIG. 2. The diagnostic beams may be generated by a first x-ray generator 30 and a second x-ray generator 32, respectively. A single image receiver 34 or a first and a second image receiver 34, 36 (as shown) may receive the diagnostic beams 26, 28 to generate an image from the diagnostic beams which is fed into the microprocessor 12 (as shown in FIG. 4) so that the diagnostic images may be compared to the three-dimensional image.

Figure 3:
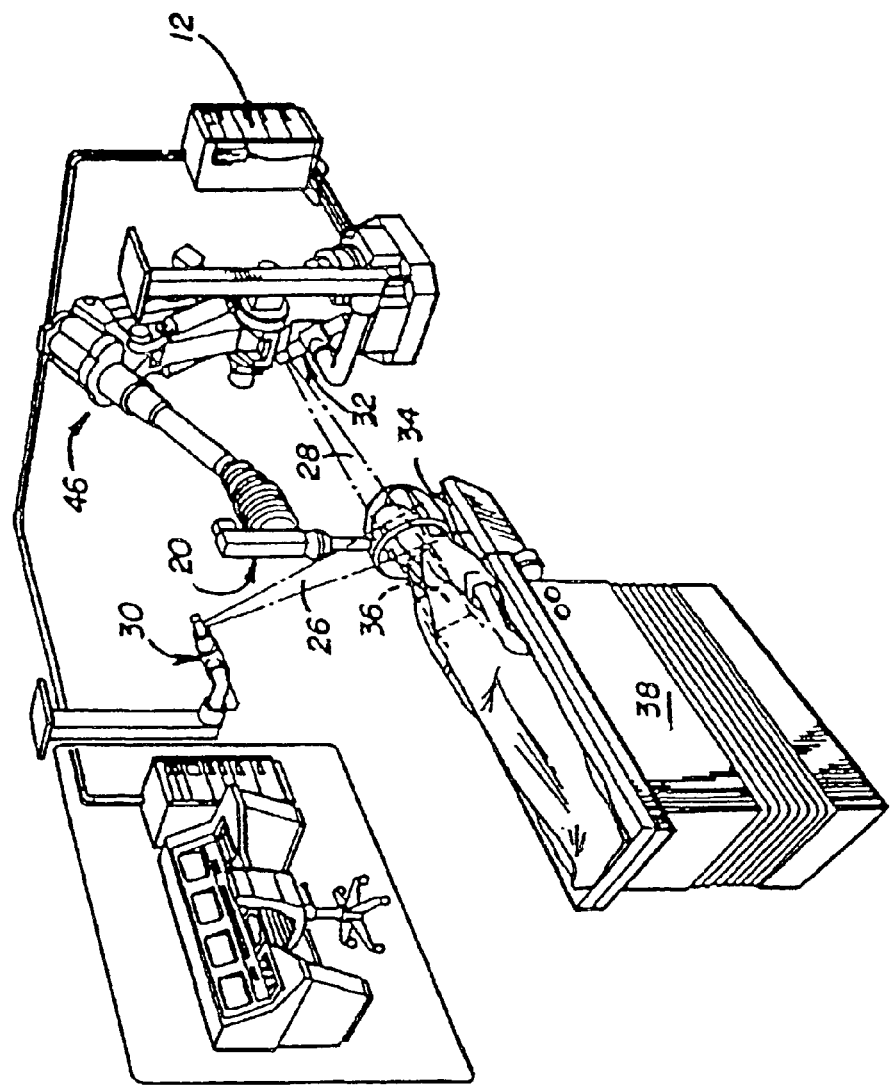
FIG. 3 is a diagram illustrating more details of the radiation treatment device.

The radiation treatment device 10 may also include a device for adjusting the relative positions of the beaming apparatus 20 and the patient 14 so that the ionizing beam is continuously focused on the target region 18. In the radiation treatment device shown in FIG. 1, the positions of the beaming apparatus and the patient may be altered with six degrees of freedom by a gantry 40 and a moveable operating table 38 with a tilting top 44. The positions of the beaming apparatus relative to the patient may also be accomplished by using a processor controllable robotic arm mechanism 46 as shown in FIG. 3 which has six axes of motion. The robotic arm mechanism permits the beaming apparatus to be moved freely about the patient's body including up, down, longitudinally along or laterally along the body of the patient.

Figure 4:
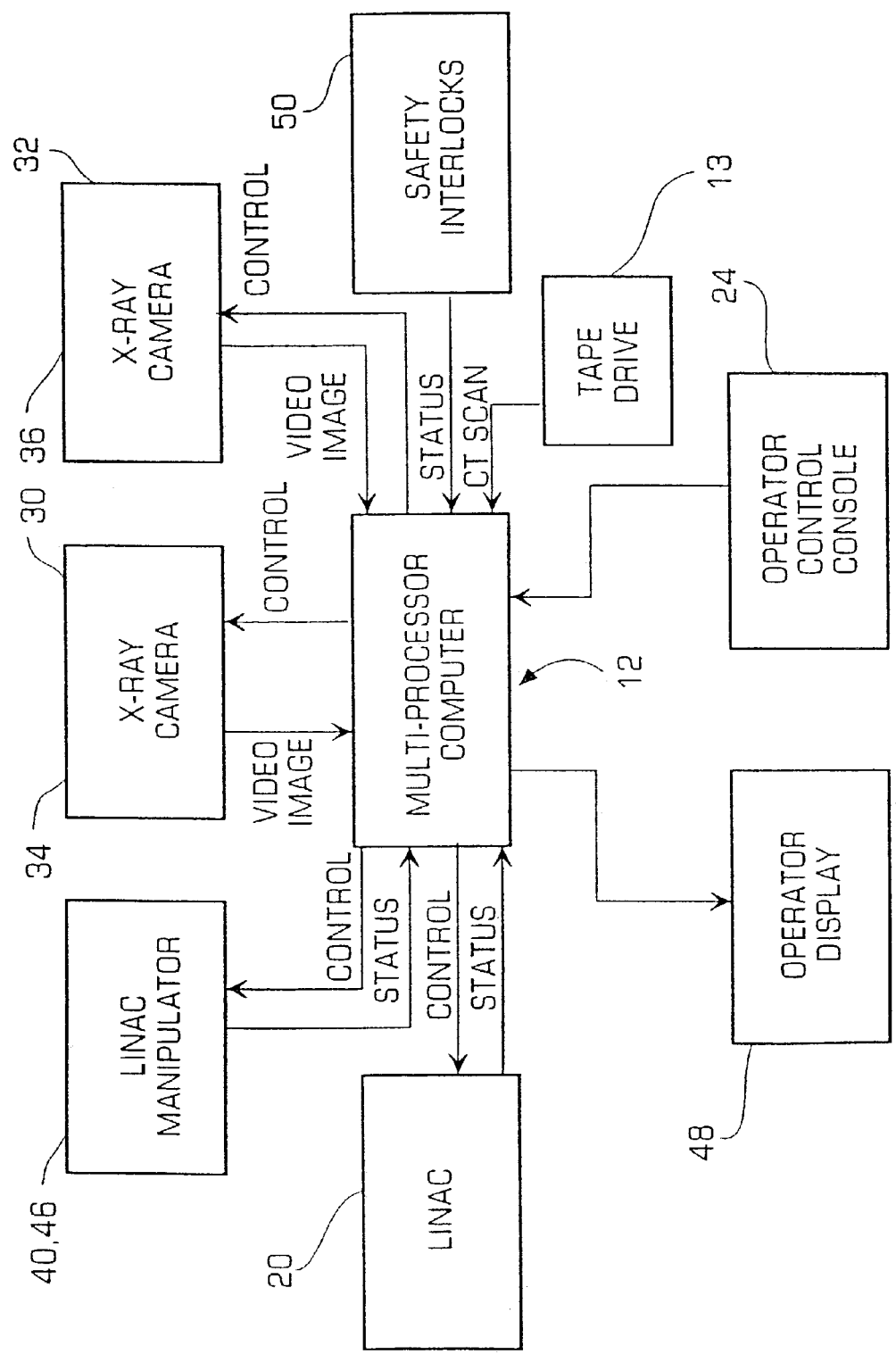
FIG. 4 is a block diagram illustrating the radiation treatment device.

FIG. 4 is a block diagram of the radiation treatment device 10 including the microprocessor 12, the tape drive 13, the beaming apparatus 20, the robotic arm 46 or the gantry 40, the x-ray cameras 30, 32, 34 and 36, and the operator control console 24 as described above. In addition, the device 10 may include safety interlocks 50 to ensure that the beaming apparatus is not activated accidentally. The device 10 may also include an operator display 48 for tracking the progress of the treatment and controlling the treatment. Any further details of the radiosurgery device may be found in U.S. Pat. No. 5,207,223 which is owned by the assignee of this application and which is incorporated herein by reference.

To accurately target the area to be irradiated in radiation therapy or radiosurgery, it is necessary to determine with high precision where the target is located during treatment. The above radiosurgery device may be ideally used for the treatment of brain or head tumors since the brain is fixed with respect to a rigid skull. The radiosurgery device may also be used with other fixed target regions in which it is easy to ensure that the ionizing beam strikes the target region, but not surrounding healthy tissue. If the target is adjacent to the diaphragm, however, the target will move during treatment due to breathing of the patient. The lung and other organs will move when the patient breathes or whenever the patient moves during the treatment. Therefore, it is desirable to provide an apparatus and method that follows a moving target region during a variety of different treatments, including radiation treatment. The apparatus may compensate for movements of the target region caused by breathing of the patient as well as movement of the target region caused by other movements of the patient.

In accordance with the invention, to determine the position of an internal moving target region such as an internal organ, external and internal markers (landmarks) may be used, as described below, and a model of their relative motions based on a series of images is determined prior to treatment. During treatment, little information is available on the placement of the internal landmarks except when the internal markers are periodically imaged using invasive devices, such as x-rays. However, the position of the external markers or a video image of the chest and/or abdomen may be determined with high precision and speed. Similarly, external sensors can provide measurement data in real time, i.e., at very high speed. Thus, the position of the external landmarks may be used in real time during treatment by inferring the placement of the internal (exact) markers by referencing the pre-operative model of the relative motion of internal and external markers. For verification, the placement of the internal markers can be determined periodically during treatment. An apparatus that compensates for breathing and other patient motion in accordance with the invention will now be described.

Figure 5:
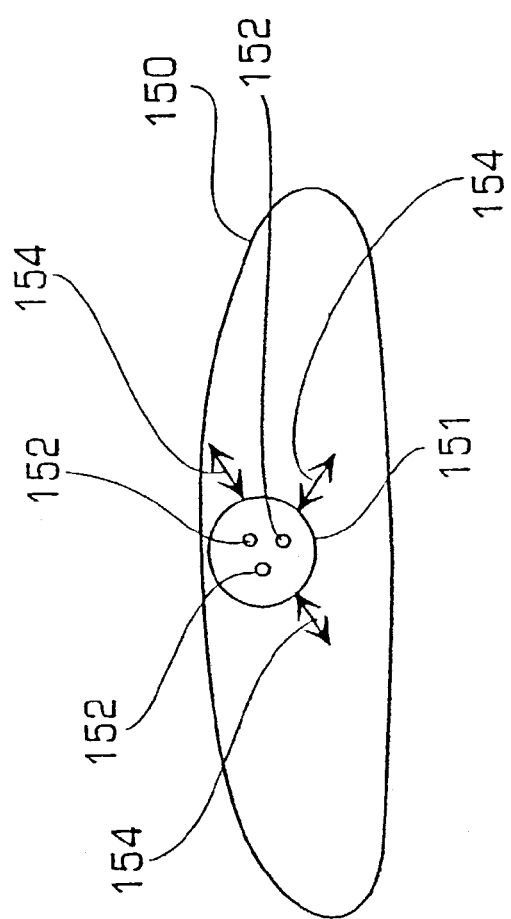
FIG. 5 is a diagram illustrating internal markers on a target organ moving as the target organ moves.

FIG. 5 is a diagram illustrating a set of internal markers 152 in accordance with the invention placed on a target organ 151 within a body 150 of the patient. The moving target organ 151 may be, for example, an organ near the diaphragm such as a lung or a liver which may move as the patient moves or as the patient inhales or exhales. In accordance with the invention, it is desirable to be able to track the motion of the target organ so that the treatment, such as ionizing radiation, is applied to the target organ and not to the healthy surrounding tissue. To track the movement of the target organ 151, the one or more internal markers 152 may be attached to or placed near various locations on or near the target organ 151. Then, as the target organ moves, the internal markers also move as shown by arrows 154. From the placement of the internal markers, it is possible to precisely determine the position of the target organ. In a preferred embodiment, more than one internal marker may be used in order to measure the movement of different areas of the target organ and the internal markers may be made of gold so that, although the internal markers are not visible outside of the body, the internal markers may be viewed using an imaging technique, which may preferably be stereotaxic x-ray imaging, but may also be ultrasound.

To track the moving target, the therapeutic beam may be moved by a robot arm or the patient couch may be moved. In the alternative, the beam may be moved by moving the leaves of a multileaf collimator or the beam may be switched off and on periodically such that the target is in the beam path, whenever the beam is on.

Figure 6:
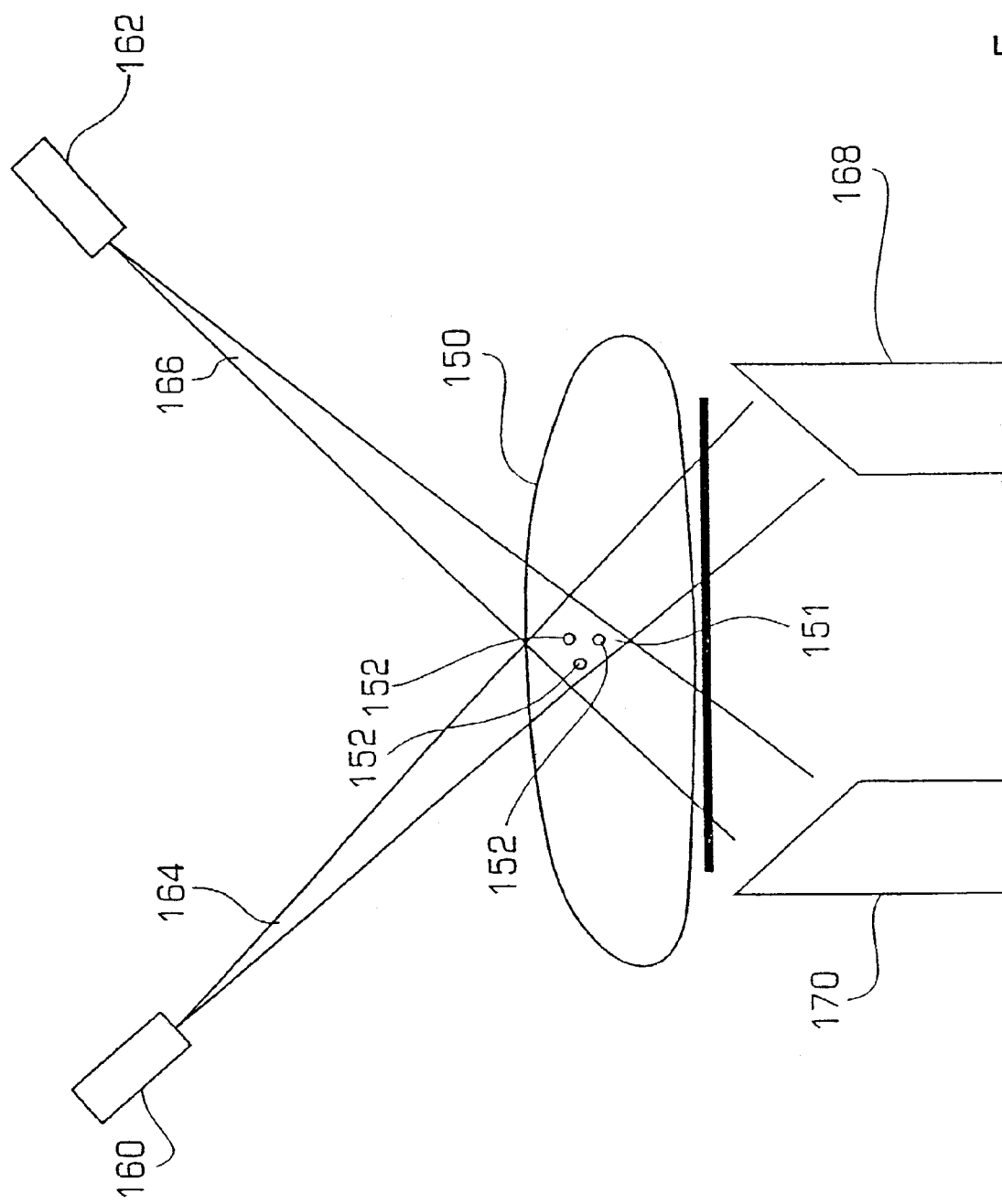
FIG. 6 is a diagram illustrating one or more internal markers attached to the target organ being imaged by x-ray devices.

FIG. 6 is a diagram illustrating one or more internal markers 152 attached to the target organ 151 being imaged by a stereotaxic x-ray device. As shown in FIG. 6, the internal markers 152 on the target organ 151 may be imaged by a first x-ray source 160 and a second x-ray source 162 which are positioned at some predetermined angle with respect to each other similar to the diagnostic x-ray beams shown in FIGS. 1-3. The x-ray sources may generate a first and second diagnostic x-ray beam 164, 166 which pass through the target organ 151 near the internal markers 152 and are received by a first and second x-ray receiver 168, 170, respectively, which receive the x-ray beams and generate an electrical signal corresponding to the received x-rays. The stereotaxic x-ray device permits the precise location of the internal markers 152 to be determined by analyzing the images generated.

Figure 7D:
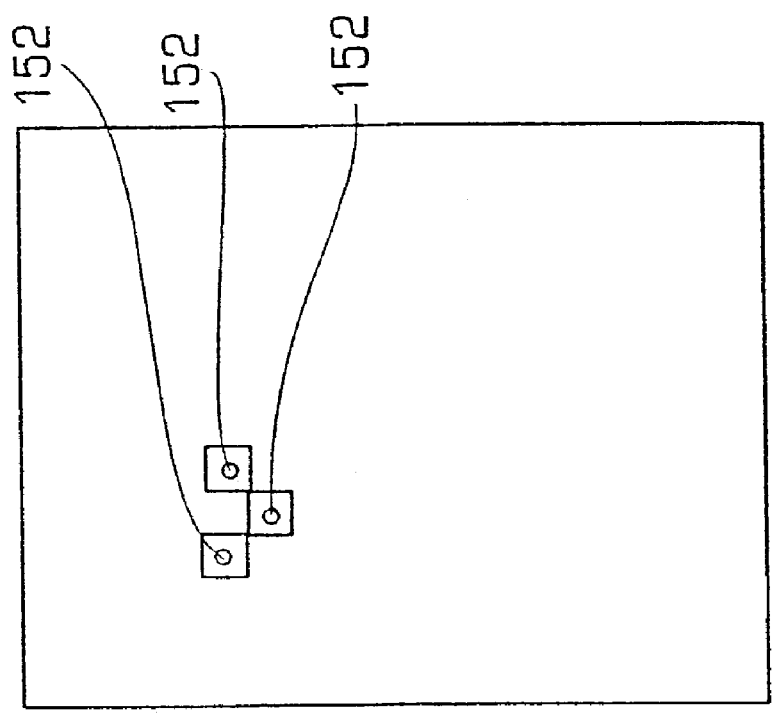
Figure 7C:
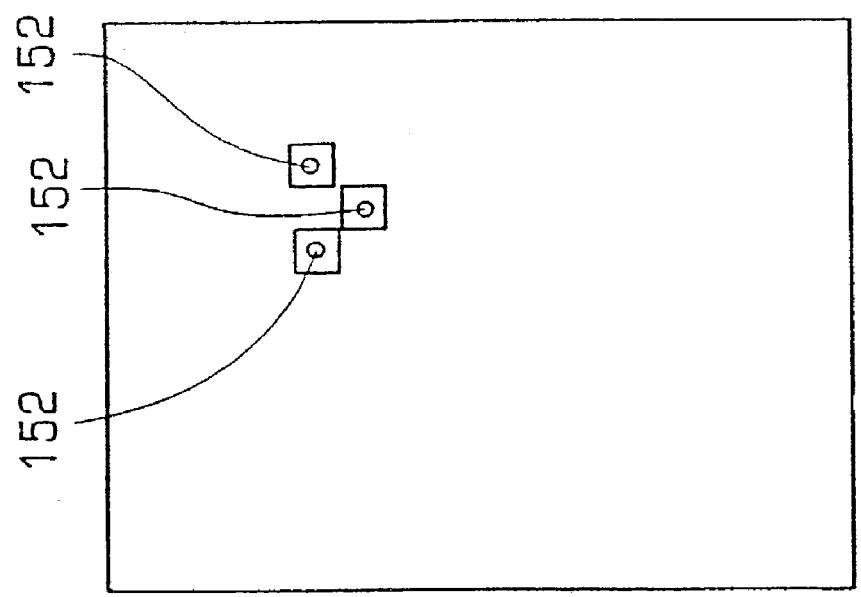

FIGS. 7A-7D are diagrams illustrating examples of the x-ray images of a target organ that include the internal markers 152 in accordance with the invention. FIGS. 7A and 7C show the same x-ray image with the internal markers 152 unenhanced and with the internal markers 152 being computer enhanced, respectively. Similarly, FIGS. 7B and 7D also illustrate the same x-ray image with unenhanced internal markers and computer enhanced internal markers, respectively. Thus, the stereotaxic x-ray imaging permits the precise location of the internal markers to be determined. The problem is that, using the stereotaxic x-ray device, internal marker positions may be determined only at predetermined intervals during treatment. In particular, the interval between imaging of the internal markers is necessary in order to limit the patient's exposure to the radiation and because the treatment beam can not be activated while the x-ray diagnostic imaging occurs. However, determining the exact position of the target organ periodically is not sufficient in order to accurately compensate for breathing and other motions of the patient. Therefore, one or more external markers may be placed on the skin of the patient near the target organ in accordance with the invention as will be described with reference to FIG. 8.

FIG. 8 is a diagram illustrating the target organ 151 within a patient's body 150 having internal markers 152 in combination with one or more external markers 180 attached to the skin of the patient in accordance with the invention. The one or more external markers 180 that are attached to the skin of the patient permit the motion 182 of the abdomen or chest wall to be determined. In the example of the breathing of a patient, the external marker 180 may track the external motion as the patient inhales and exhales. The external markers 180 may be automatically tracked with a number of optical methods, such as infrared or visible light, and the position of the external marker may be determined more than 60 times per second. The external markers may also be attached to the belt, the skin itself, a flexible ring or a vest which fits around the waist of the patient.

If only external markers are used to compensate for the motion of the patient, however, they cannot accurately reflect the internal motion of the target organ since the target organ may move a small amount while the external marker may move a larger amount and vice versa. The external markers are not sufficiently precise to compensate for the motion of the patient. Therefore, the combination of the internal markers and the external markers is necessary in order to accurately track the motion of the target organ. Thus, the periodic x-ray imaging of the internal markers is synchronized with the continuous optical tracking of the external markers to provide accurate tracking of the motion of the target organ. In order to synchronize the motion of the internal and external markers, it is necessary to determine the relationship between the positions of the internal and external markers which may occur at the start of the treatment process and will be described below with reference to FIG. 10.

When some movement of the target organ is detected, the treatment system, such as the radiosurgery device described above, may compensate for the movement in a number of different ways. For example, the treatment system may move the treatment device, such as the beaming apparatus 20, relative to the patient or vice versa. The treatment system may also move a shaping or collimating device that is within the path of the treatment device to change the characteristics of the treatment device. The treatment system may also only activate the treatment device when the target organ is within the treatment path or block the treatment device when the target organ is not within the treatment path. Now, one of the benefits of the motion compensation apparatus in accordance with the invention will be illustrated and described.

Figure 9B:
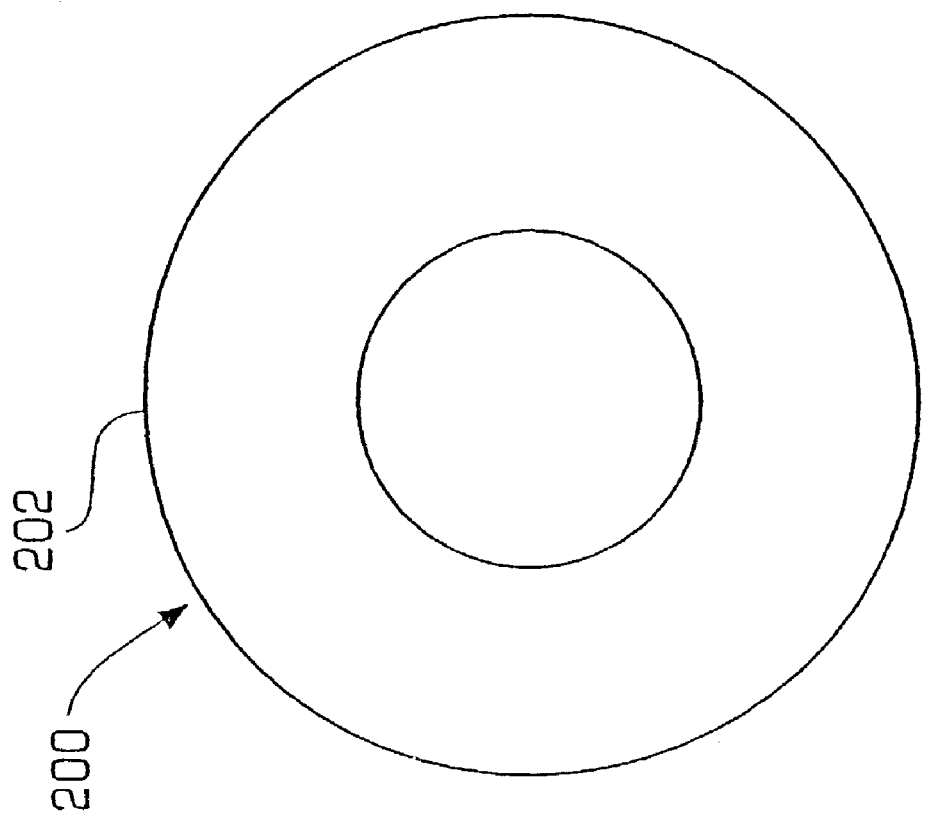
FIGS. 9A-9D are diagrams illustrating the reduction in the safety margin in accordance with the invention.
Figure 9A:
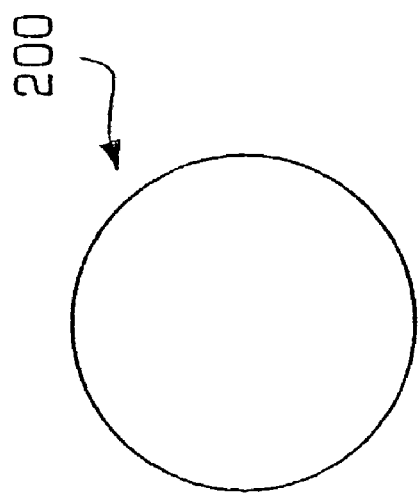
Figure 9D:
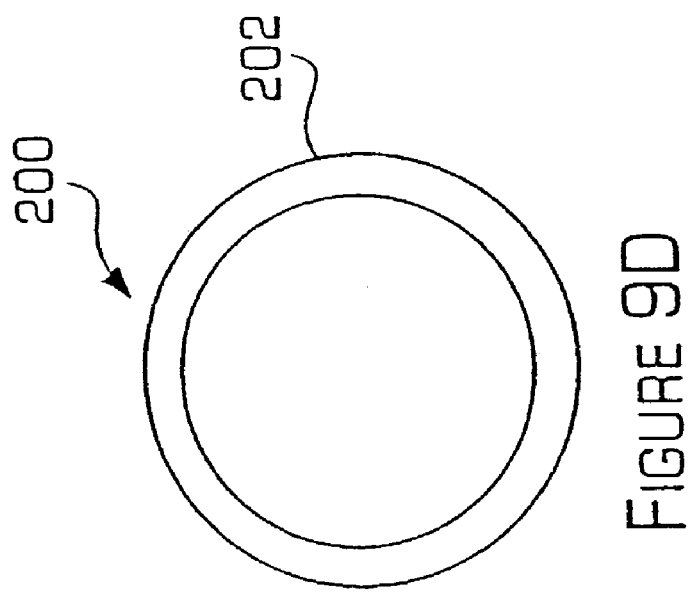
Figure 9C:
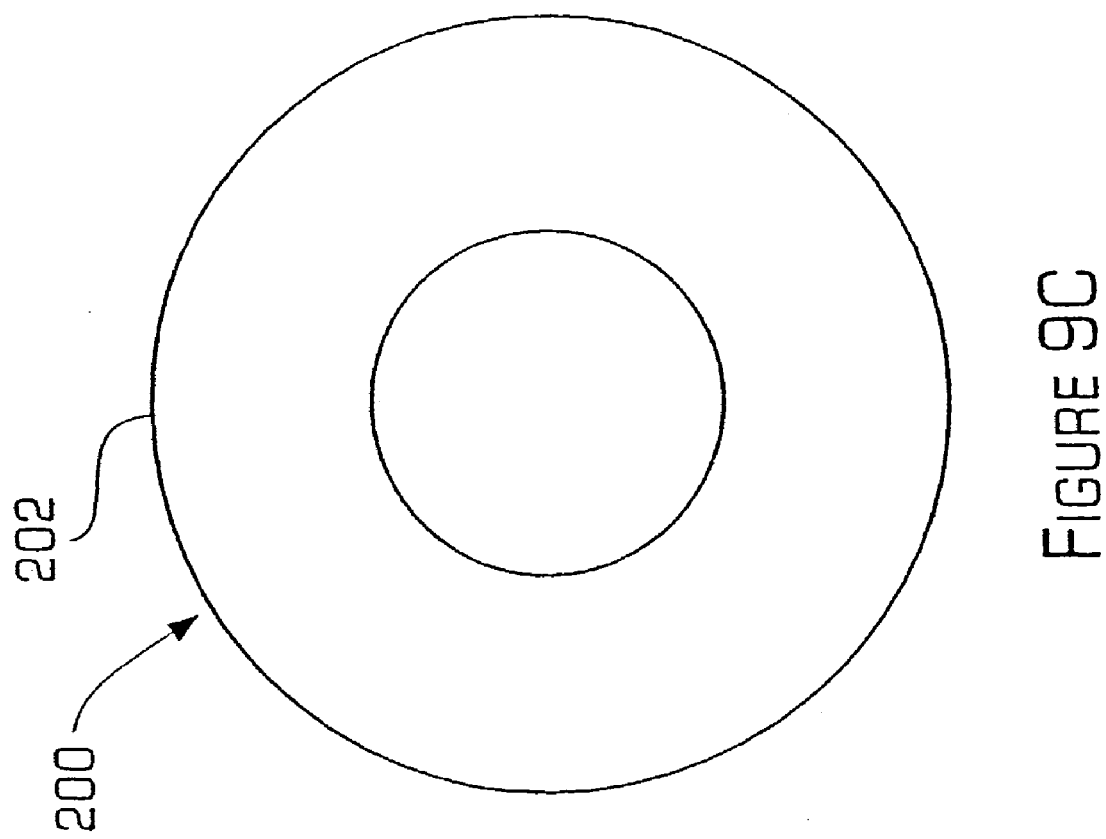

FIGS. 9A-9D are diagrams illustrating one benefit of the motion compensation apparatus in accordance with the invention. In particular, FIG. 9A shows a volume of target region, such as a tumor, to be treated 200 without a safety margin. In particular, the volume may have no safety margin provided that the position of the target region to be treated is precisely known so that healthy tissue is not damaged. If the position of the target region cannot be exactly determined, such as for a moving target organ due to breathing and other patient motion, the volume 200 requires a safety margin 202 as shown in FIG. 9B. The problem with the safety margin is that the required volume of irradiation increases very rapidly with the diameter of the target. For example, for a spherical target the ratio between the diameter of the target and the required dose is cubic. The safety margin 202 for a typical radiosurgery device is shown in FIG. 9C. FIG. 9D shows the much reduced safety margin 202 which is possible due to the motion compensation apparatus and method in accordance with the invention. A reduction of the safety margin by a factor of two results in a volume reduction of the dose by a factor of eight. Thus, the unwanted dose to healthy tissue may be reduced by a factor of four while the dose to the target organ or tumor may be doubled. For a large variety of cancer cases with particularly grim prognosis, the motion compensation apparatus in combination with typical radiosurgery devices can greatly improve the efficacy of the treatment. Now, a method for motion compensation during treatment in accordance with the invention will be described.

Figure 10:
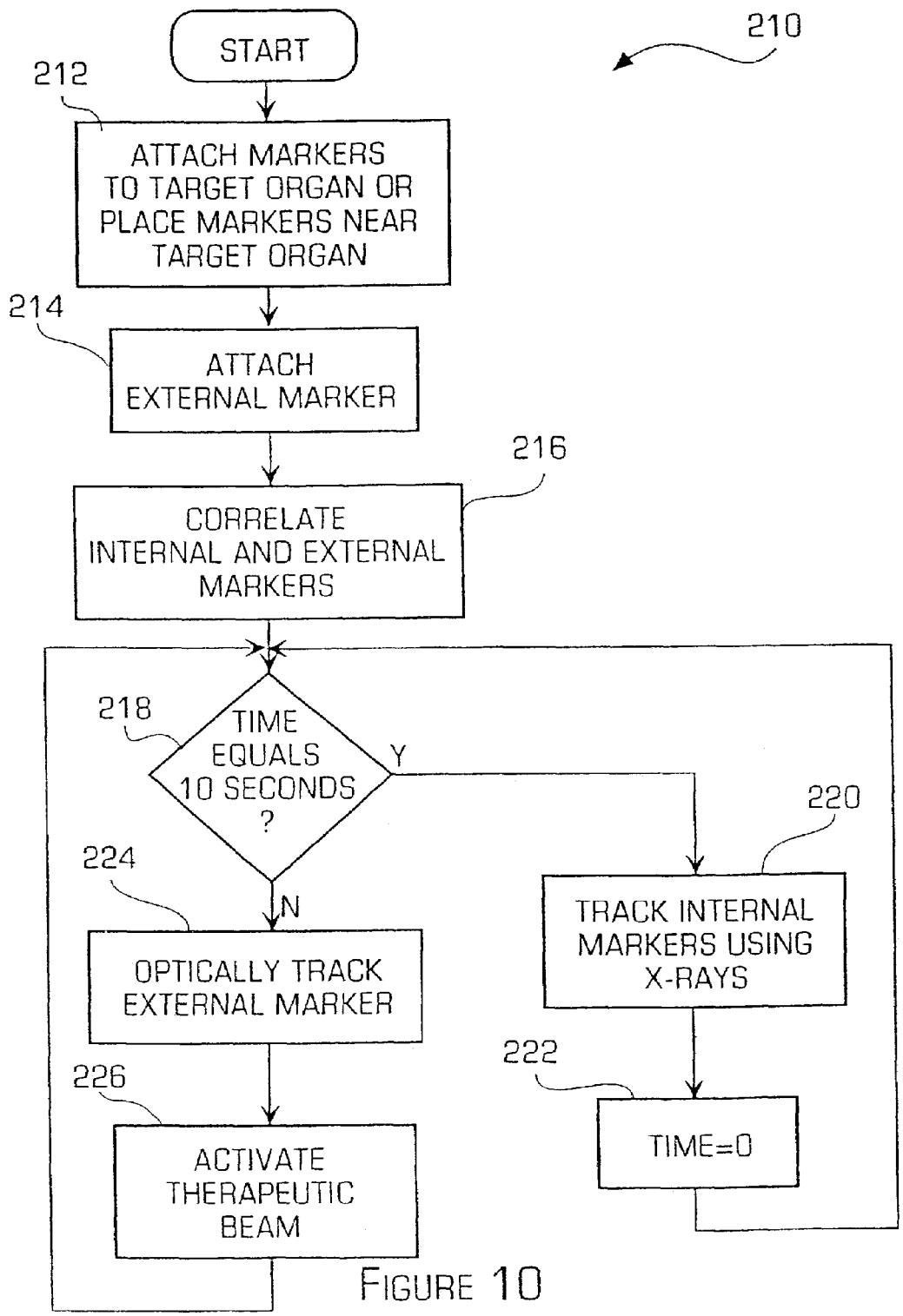
FIG. 10 is a flowchart illustrating a method for compensating for breathing and other motion in a radiosurgical device.

FIG. 10 is a flowchart illustrating a method 210 for compensating for breathing and other motion of a patient during treatment, such as with a radiosurgical device. The first few steps in the method may be performed at a time prior to the actual treatment of the patient. In particular, a surgeon may attach a set of internal markers in the proximity of or within the target organ during a short surgical procedure in step 212 and then, just prior to treatment, the surgeon may attach a set of external markers to the chest or abdominal wall of the patient near the target organ in step 214. Next, the processor of the radiosurgery device correlates the position of the internal markers and the external markers in step 216 just prior to starting the treatment of the patient. The method for correlating the internal markers with the external markers is described below with reference to FIG. 11. Once the positions of the internal and external markers have been correlated, the treatment of the patient may begin.

First, the apparatus determines if the total elapsed time since the last time the internal markers were imaged is equal to a predetermined number of seconds. The predetermined number of seconds is preferably between two and ten seconds and more preferably about ten seconds. If the total elapsed time is equal to the predetermined number of seconds, then the treatment beam is deactivated and the internal markers are imaged using, for example, stereotaxic x-ray imaging in step 220. Next, the total elapsed time is reset to zero and the method returns to step 218. Thus, in accordance with the invention, the internal markers are imaged every predetermined number of seconds. Returning to step 218, if the total elapsed time is not equal to the predetermined number of seconds, then the external markers are optically tracked in step 224 while the treatment beam is activated in step 226. The external markers may be tracked so that position data is provided to the processor of the radiosurgery device as much as sixty times per second. The processor may then correlate the position of the external markers with the internal markers and generate positional data about any change in the position of the target organ. Thus, between the periodic imaging of the internal markers, the position of the external markers is used to track the position of the target.

When some movement of the target organ is detected, the treatment system, such as the radiosurgery device described above, may compensate for the movement in a number of different ways. For example, the treatment system may move the treatment device, such as the beaming apparatus 20, relative to the patient or vice versa. The treatment system may also move a shaping or collimating device into the path of the treatment device to change the characteristics of the treatment beam. The treatment system may also only activate the treatment device when the target organ is within the treatment path or block the treatment device when the target organ is not within the treatment path. Now, a method for correlating the positions of the internal and external markers in accordance with the invention will be described.

Figure 11:
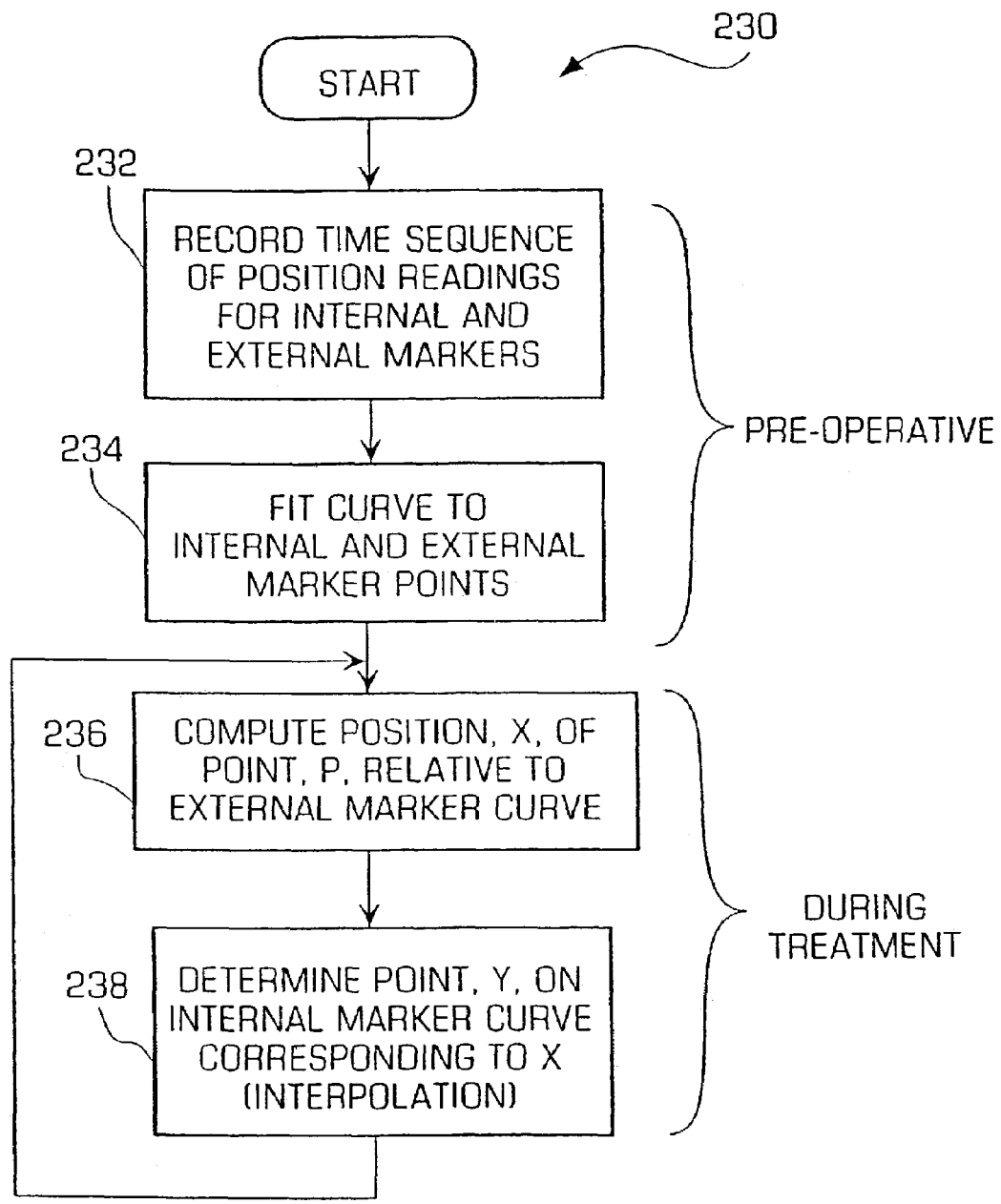
FIG. 11 is a flowchart illustrating a method for correlating the internal and external markers in accordance with the invention.

FIG. 11 is a flowchart illustrating a method 230 for correlating the positions of the internal and external markers in accordance with the invention. Several steps of the method occur during the pre-operative process while several steps occur during the actual treatment. In particular, in step 232, a series of time sequence images are generated for both the internal and external markers throughout the respiratory cycle so that a plurality of points corresponding to the internal and external markers are generated during the pre-operative phase. The plurality of points corresponding to the external markers and the internal markers may each be referred to as a point cloud. Next, the processor in the radiosurgery device may fit a curve to the points generated for the internal markers and a separate curve to the points generated by the external markers in step 234. These curves permit the positions of the external and internal markers to be correlated to each other.

During the actual treatment, the system generates a position, x, of the external markers by a technique, such as infrared imaging, at a particular time and that position, x, is fit to the previously generated curve of the external marker positions in step 236. Next, in step 238, a position, y, of a point on the internal marker curve which corresponds to the position, x, is determined by comparing the two curves which is a process known as interpolation. This process may be performed for each marker. Using this method, the position of the external markers may be correlated to the position of the internal markers which permits the system to accurately determine the amount of movement of the target organ without actually imaging the internal organ. Another way to perform the correlation of the positions of the internal and external markers is to use a neural network trained to perform interpolation or other known mathematical interpolation methods for establishing the correspondence between the internal and external markers after having computed the point clouds.

Now, various other embodiments of the method for compensating for breathing and other patient motion in accordance with the invention will be described. In all of these embodiments, the respiratory and diaphragmatic excursion may be limited and minimized by binding the abdomen or compressing the abdomen. In a first embodiment, one or more small metal markers (also known as landmarks) are attached to the target organ before treatment. There may be three or four metal markers with possibly distinct shapes or sizes, which may be, for example, small gold beads. The exact position of these internal markers is determined by two x-ray cameras, which acquire a stereo image of the target site. There may also be one or more infra-red probes which are attached to the patient's skin surface. The infra-red probes give a very accurate and high speed position reading, but they only show the surface of the patient's body. In this embodiment, internal imaging of the internal markers and external imaging of the external markers (i.e., x-ray imaging and infrared imaging) are combined. In particular, prior to treatment, a series of images with both modalities (i.e., x-ray and infrared, respectively) is obtained. For these images, the time of image acquisitions is recorded, or at least the images with both modalities are acquired simultaneously so that the time of image acquisition does not vary by more than approximately 0.01 sec. In this way, a series of pre-operative images of both external and internal landmarks is acquired where each image has a time-stamp. These series of images determines a model of the relative motion between internal and external landmarks as described above.

During the actual operation, it is difficult to obtain x-ray images more than once every predetermined number of seconds due to concerns about exposing the patient to too much radiation and due to the fact that the treatment beam cannot operate when x-ray imaging is being done. The x-ray imaging alone would therefore be too slow to follow breathing motion with high precision. Therefore, the external landmarks on the skin surface, as seen by the infrared system, are used for intra-operative localization, where we continuously reference the previously computed model of relative motions of the internal and external markers. This allows the exact placement of the internal landmarks (gold beads) to be predicted at time points where no x-ray images are available. Now, a second embodiment of the method will be described.

In a second embodiment, there are situations in which it is desirable to compensate for respiratory motion as well as to compensate for pulsation effects. These pulsation effects may cause motions of the patient in much the same way as respiration does. In accordance with the invention, a strain gauge or some other type of pulsation measurement device captures the current state of pulsation of the patient. A device for measuring the pulsation movement may, for example, be a device for recording electrocardiograms, or similar devices used for monitoring patient-specific data in an intensive care unit. Another device may be fit to a patient's wrist and detect the state of aortic pulsation via tactile information. As above, one or more time stamps may be used to obtain a pulsation motion pattern representing the internal target motion caused by the pulsation effects. Thus, by using a sensor for observing the external effects of respiratory motion, we can compensate for both respiratory motion and pulsation motion at the same time. Now, a third embodiment of the invention will be described.

In a third embodiment of the method in accordance with the invention, no internal landmarks attached to the target organ are used. Instead, an ultra-sound camera is used to acquire the pre-operative image series, again in combination with an infra-red tracking system. The infra-red system in this embodiment establishes both the position of the external landmarks and the position of the (movable) ultra-sound camera, which must be moved by a human operator during this pre-operative phase. During the pre-operative phase, the ultra-sound images may be analyzed manually or semi-automatically in order to locate the target. During treatment, the external landmarks (infra-red probes) are used to compensate for the motion of the target organ since the motion model we have established allows the determination of the position of the internal target organ from the position of the external markers.

Furthermore, there are situations, where the attachment of markers to an anatomic target is difficult, undesirable or costly. In many cases, such fiducials are necessary, because the target tumor itself is not well visible in x-ray images. However, in some cases the tumor is partly visible in an x-ray image at least for a human operator. In such cases, the method described above may be used without placing such internal markers. This can, for example, occur for larger peripheral tumors of the lung, or also for certain tumors of the liver.

If the tumor is visible in x-ray images, the method may proceed as follows. Instead of using internal markers, the target is manually or semi-automatically delineated in the x-ray images while it is displayed on a computer screen, for example. From this delineation, one can compute the exact placement of the target tumor at the time point when the x-ray image were taken. To perform this computation, the two-dimensional contour of the tumor, as determined by the delineation, is matched to the three-dimensional shape of the target, as known from the preoperative tomography. The time stamps of the external markers are now used as above to form a model for the correlation between the internal and external motion. To help the process of delineation on the computer screen, the contour of the three-dimensional target shape may be projected onto the x-ray image displayed on the screen so that only alignment is necessary.

In the case of ultrasound being used a one of the sensors, the problem of placing the ultrasound camera on the patient's body arises since the ultrasound signal should not travel through air. In addition, the ultrasound cameras must be moved during treatment by an experienced operator to ensure (1) that the tumor is within the field of view of the camera; (2) that the tumor is visible with sufficient clarity in the image; and (3) the signal should not travel in air. To accomplish this, a movable ultrasound camera, placed on a cushion filled with liquid either performs periodic or regular motion, or the motion of the ultrasound camera is controlled by an operator from outside the operating room. The operator moving the ultrasound camera must remain outside the treatment room, due to the presence of radiation in the treatment room. The step of moving the ultrasound camera from outside the room can be accomplished by attaching ultrasound sensors to a small robot arm. To move the ultrasound camera, the operator moves this robot arm via a control wand or joystick, or a computer mouse pointer. Now, more details of the ultrasound treatment system will be described.

Figure 12:
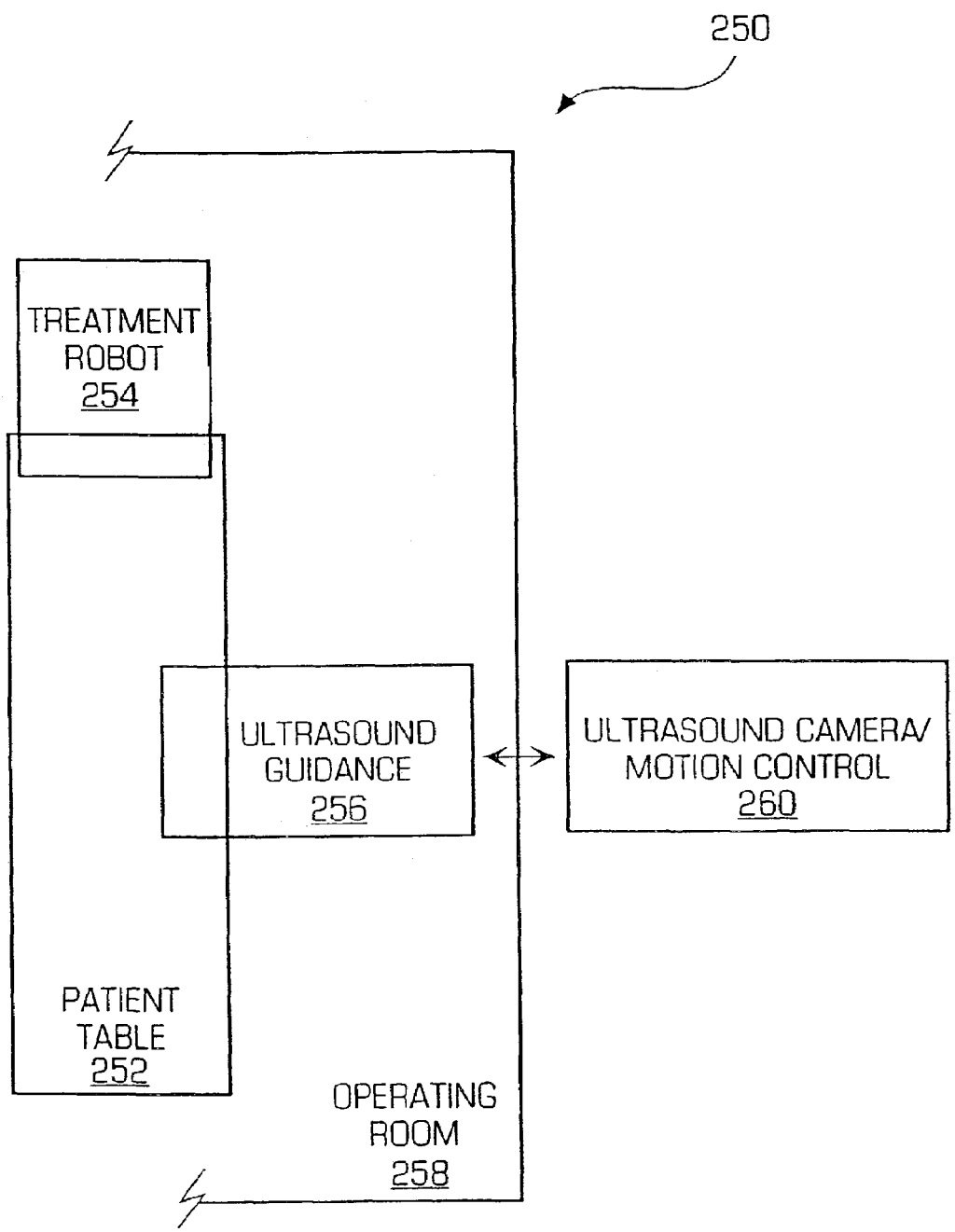
FIG. 12 illustrates an example of an ultrasound system in accordance with the invention.

FIG. 12 is a diagram illustrating an example of a ultrasonic treatment system 250 in accordance with the invention wherein an ultrasound sensor may be used for determining the position of a target region in a patient. In this example, the ultrasonic sensor may be remotely controlled by an operator. In particular, as shown, a patient table 252, a treatment robot 254 that generates the therapeutic beam and an ultrasound guidance system 356 may be located in an operating room 358. Then, an ultrasound camera and motion control system 260 may be located remote from the operating room due to the radiation present in the operating room. In operation, an ultrasound specialist may move the ultrasound camera from outside of the operating room. Now, a method for marking a target region using the examplary ultrasound system will be described.

Figure 13:
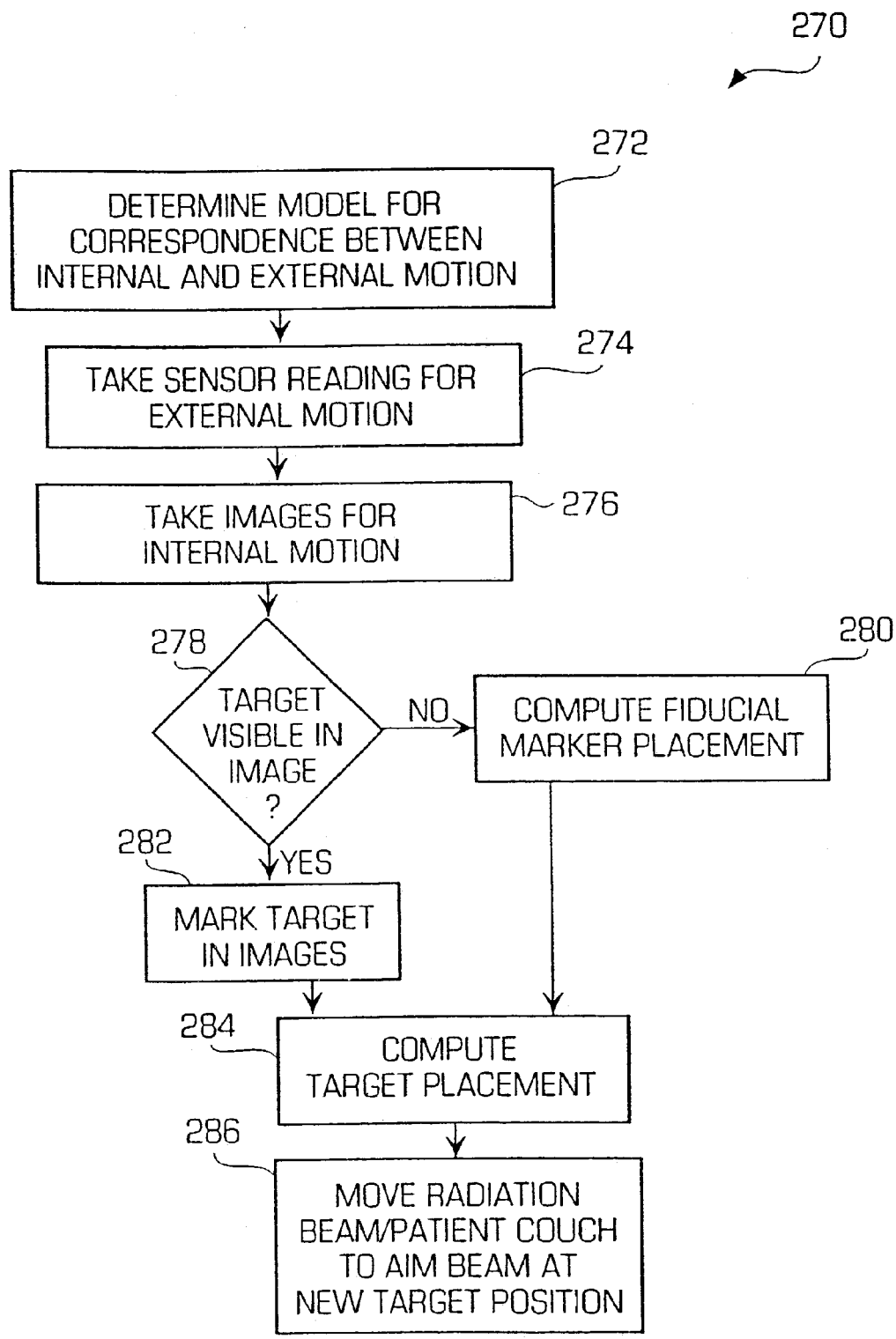
FIG. 13 is a flowchart illustration an example of an ultrasound treatment method in accordance with the invention.
Figure 14:
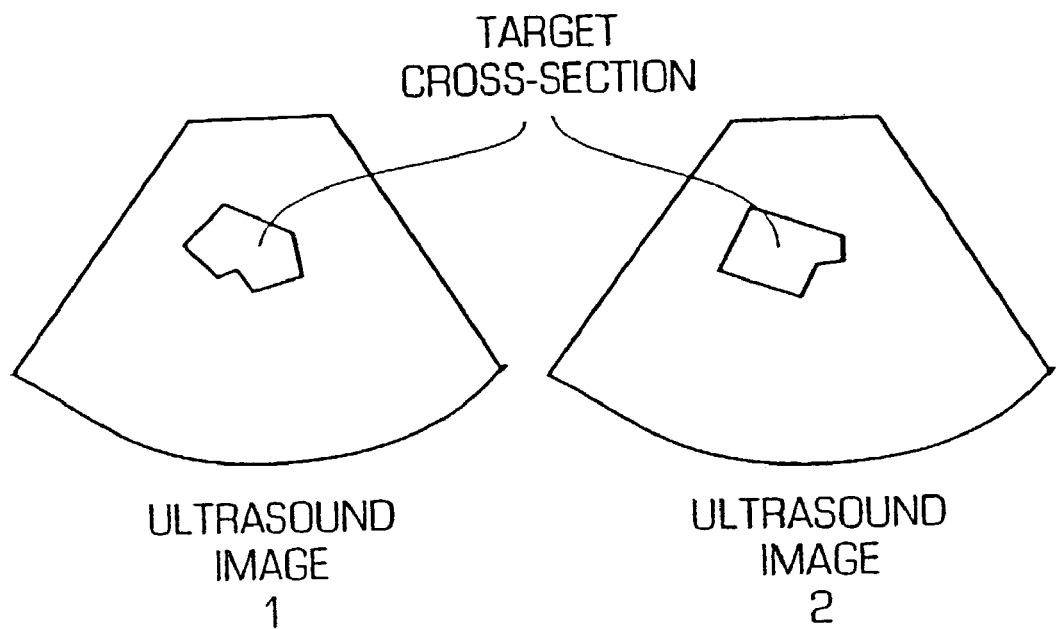
FIG. 14 is a diagram illustrating the process for manually marking the target using ultrasonic image pairs in accordance with the invention.
Figure 15:
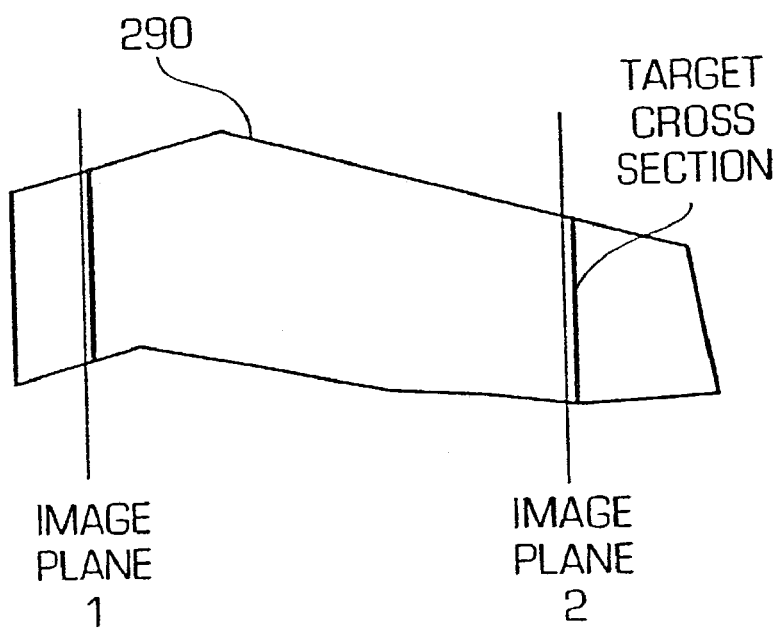
FIG. 15 is a diagram illustrating the automatic alignment of the marked target region with a preoperative image of the target region.

FIG. 13 is a flowchart illustrating a method 270 for marking and treating a target region using ultrasound in accordance with the invention. In particular, in step 272, a model for the correspondance between the internal motion and the external motion is determined as described above in more detail. In step 274, a sensor reading to determine the external motion is taken and in step 276, an ultrasound image for determining the internal motion is taken. In step 278, it is determined by the ultrasound operator if the target is visible in the ultrasound image. If the target region is not visible in the ultrasound image, then the position of the internal fiducial markers is determined in step 280. If the target region is visible in the ultrasound image, then the target region is marked in the ultrasound images in step 282. In step 284, based on the fiducial position or based on the target region marked in the ultrasound images, the position of the target region is determined. In step 286, the radiation beam or the patient couch is moved to aim the beam at the new target position. Thus, the ultrasound images may be used to locate the current position of the target region or the position of the fiducials may be used. FIG. 14 illustrates a target region 290 being imaged by two ultrasound images wherein each ultrasound image shows a cross-section of the visible target region. FIG. 15 illustrates those ultrasound cross-sections being used to determine the position of the target region by matching the cross-sections with the pre-operative target region image. To prevent the small robot (carrying the ultrasound camera) from applying undesired forces (too much pressure) on the patient's body, a force sensor may be attached to the small robot. This force sensor stops or reduces a motion of the robot directed into the patient's body.

Another embodiment is very similar to the third embodiment except that a device for measuring the air flow may be used instead of the ultrasound camera. The device may be a mouthpiece that records the direction and volume of airflow and correlates these measurements with the location of the internal fiducials or any other mechanism for detecting the location of the internal organs. In this embodiment, a reference position of the target organ, such as a lung, such as at full exhalation or at full inhalation or any intermediate respiratory state may be used to correlate the current respiratory state to a state imaged prior to the treatment so that the motion and position of the target organ may be determined during the treatment and the position of the treatment device may be moved based on the determined motion of the target organ. Now, a fifth embodiment of the invention will be described.

In yet another embodiment of the invention, a slightly different technique is used. In particular, during most radiation treatments, the patient is awake and conscious so that it is often difficult to determine whether a motion observed by real-time tracking of external markers is indeed due to breathing and not to other small movements of the patient's body. Such other movements of the body may be caused, for example, by sneezing or other sudden motions. To detect and accurately track these other motions, a pair of x-ray cameras in addition to the ultrasound camera described above may be used. In this embodiment, the ultra-sound camera is only used before the operation to determine the correlation between the target motion and the motion of external landmarks as described above. Thus, a series of pre-operative images is again acquired to determine the relationship between the motion of the patient's skin surface and the target organ. During treatment, the x-ray cameras may be used to determine sudden motion of the patient based on well known computer methods for automatically finding bony landmarks in x-ray images. These x-ray images may be compared to pre-operative tomographic images (CT or MR images) to determine sudden movement of the patient.

In more detail, it may be necessary to distinguish between patient shift, caused by voluntary motion or by sneezing on the one hand, and respiratory motion on the other hand. These two types of motion must be processed in different ways. For example, a voluntary sideward motion of the patient should result in a shift of the entire deformation model whereas normal respiration should not shift the entire deformation model and only the beam should be moved accordingly. To distinguish the two types of motion, the system may, at each time point at which both an internal sensor and an external sensor reading is available, calculate the inferred internal position from the current deformation model. The system may then compare the actual position to the inferred position and any deviation exceeding a fixed threshold value will lead to a recomputation of the entire deformation model (implying a detection of a patient movement instead of respiration). After the recomputation, the treatment may resume. Thus, in accordance with the invention, the system may detect a patient movement other than respiration and therefore stop to recompute the deformation model before recommencing the treatment. If the movement is respiration movement, the treatment continues since that motion is compensated for by the deformation model.

In yet another embodiment of the invention, the system described may be used to track deformation and/or squeezing of a target region. For example, in some cases the target region, such as a tumor, can be squeezed/deformed by respiration to some extent. In this case, the system may detect such squeezing/deformation by the motion of the internal fiducials as described above. As described above, interpolation between the different relative placements of the internal fiducials allows the system in accordance with the invention to determine the current deformation state of the tumor so that the treatment can take into account the current deformation of the target region and deliver a better, more focused treatment.

In accordance with the invention, it may also be desirable to acquire several preoperative three-dimensional (tomographic) images of the target region and obtain preoperative information about the deformation or squeezing of the target region during the respiratory cycle. In particular, each such squeezing or deformation state of the tumor is characterized by a specific relative placements of the fiducial markers. During the operation, this relative placement of the fiducials may be used to compute the current deformation state of the target region at individual time points so that the target region may be compensated for in accordance with the invention since this deformation information may be readily incorporated into the motion pattern correlating the external to internal motion as described above.

In some cases, it is desirable to use a simplified model for the correlation between the internal and the external motion, i.e. motion of the target and motion of the skin surface, since that motion is fairly easily modeled. Typically, such a model for motion correlation in accordance with the invention is computed from several image pairs showing the current placement of the target at the corresponding time points and a series of matching sensor readings for the placement of the patient's skin surface. However, in accordance with the invention, the model for the motion correlation can also consist of a single time point where the patient is instructed to return to the position corresponding to this time point and where irradiation only takes place while the patient's respiratory state corresponds to this position as controlled by the computer system.

To address patient shift or a systematic drift of the patient during irradiation in accordance with the invention, the deformation model representing correlation between the internal and the external motion must be recomputed during treatment. In some cases, it is undesirable to interrupt the treatment for such recomputation. To avoid such interruption, the system may generate a very small number of snapshots (showing both external and internal sensor readings). During treatment, new snapshots (showing both sensor readings) may be generated. The system may then perform a continuous real-time update of the deformation model. Thus, for each new snapshot, the entire model for the correlation is recomputed based on a small set of the most recent snapshots.

In accordance with another embodiment of the invention, a general model for the correlation between the internal and external markers may be generated. As described above, a specific model for the correlation between internal and external motion for each individual patient is generated. In some cases, the necessity of using internal fiducial markers can be obviated by determining a general model for the correlation between the internal motion and the external motion from several patients and earlier treatment data. Using this past data, the motion of certain anatomic regions under respiration is represented by a general model since the movement of those anatomic regions does not change between patients. Then, since the general model is being used, the system only observes the external motion of the target region at periodic time intervals during treament since the internal motion may be inferred from the general model and the occasional updates.

In accordance with another embodiment of the invention, the system may compensate for system time delays. In particular, in some cases, the therapeutic beam is too slow to follow the motion of the target region since the speed of the therapeutic beam is limited by the mechanical properties of that therapeutic beam. In such cases, the data transfer between the device moving the treatment beam is not sufficiently fast to place the beam at the desired position with the desired speed. In this case, the inferred placement of the target is correct, but a systematic lag between actual and commanded placement of the therapeutic beam will occur which decreases the overall accuracy of the treatment. This problem is overcome by the system in accordance with the invention. In particular, based on our known model for the correlation between the internal motion and the external motion, the system can predict the proper placement of the internal target region. Thus, the target region location at various times during the respiratory cycle or other motion may be determined ahead of time. In addition, the system may determine the system time lag. Thus, the system may use the anticipated movement of the target region and the known time lag to compensate for the time lag by anticipating that time lag.

While the foregoing has been with reference to a particular embodiment of the invention, it will be appreciated by those skilled in the art that changes in this embodiment may be made without departing from the principles and spirit of the invention, the scope of which is defined by the appended claims.

The invention claimed is:

1. A method of compensating for motions of a patient during treatment, the method comprising:
    generating pre-operative three-dimensional images of an internal region showing an internal fiducial and a target region located in the internal region;
    acquiring an ultrasound image of the internal region, the ultrasound image showing the internal fiducial;
    matching the internal fiducial in the ultrasound image with the internal fiducial in one of the pre-operative three-dimensional images to determine a position of the target region;
    simultaneously detecting a location of an external marker coupled to the patient to indicate an external movement of the patient and acquiring a corresponding ultrasound image of the internal region during treatment; and
    generating a correlation between the external movement and the position of the target region so that the position of the target region is inferred from the location of the external marker.

2. The method of claim 1, further comprising detecting the position of the external marker using infrared imaging, visual imaging, or magnetic localization.

3. The method of claim 1, further comprising determining a position of an ultrasound camera that is used to generate the ultrasound image.

4. The method of claim 3, wherein a material filled cushion is located between the ultrasound camera and the patient to improve the ultrasound images.

5. The method of claim 3, further comprising sensing a force of the ultrasound camera into the patient and preventing the ultrasound camera from applying undesirable force to the patient.

6. The method of claim 1, wherein generating the correlation further comprises producing a deformation model for representing the correlation between the external movement and the position of the target region.

7. The method of claim 1, further comprising distinguishing between respiratory motion and another patient motion by comparing the position of the target region to an inferred position of the target region inferred from the correlation and re-computing the correlation when a deviation between the position of the target region and the inferred position of the target region exceeds a threshold value.

8. The method of claim 7, further comprising continuing the treatment without re-computing the correlation when the deviation does not exceed the threshold value.

9. The method of claim 1, further comprising generating a series of ultrasound snapshots, including the ultrasound image, to generate a correlation of an external movement of the patient and the position of the target region, generating a plurality of ultrasound snapshots during the treatment, and continuously updating the correlation during the treatment by re-computing the correlation each time one of the plurality of ultrasound snapshots is generated during the treatment.

10. The method of claim 1, further comprising computing a deformation state of the target region based on relative positions of the internal fiducial and another internal fiducial.

11. The method of claim 1, wherein generating the correlation comprises computing a deformation state of the target region based on the corresponding ultrasound image.

12. The method of claim 1, wherein generating the correlation comprises:
fitting a first curve to a first point cloud corresponding to the external marker; and
fitting a second curve to a second point cloud corresponding to the internal marker.

13. The method of claim 12, wherein generating the correlation further comprises:
locating on the first curve a first point that represents a first location of the external marker; and
finding a second point on the second curve that corresponds to the first point on the first curve.

14. The method of claim 12, further comprising time-stamping each of the points of the first point cloud.

15. The method of claim 12, further comprising predicting the position of the target region, wherein the predicting comprises:
locating on the first curve a first point that represents the location of the external marker at a first time; and
finding a point on the second curve that corresponds to a second point on the first curve, wherein the second point corresponds to a second time after the first time.

16. The method of claim 1, further comprising:
determining a respiratory pattern of the patient, wherein the external movement is a respiration movement; and
predicting the position of the target region based on the correlation.

17. The method of claim 16, further comprising dynamically moving a robotic arm coupled to an ultrasonic camera in response to predicting the position of the target region based on the correlation.

18. The method of claim 16, further comprising dynamically adjusting a direction of a treatment beam based on the predicting to compensate for a time lag between detection and adjustment, the detection being a detection of a new position of the target region and the adjustment being an adjustment of the treatment beam toward the new position.

19. The method of claim 18, wherein the compensating further comprises determining a periodicity of the respiration motion.

20. The method of claim 18, further comprising switching a treatment beam on and off according to the predicting.

21. The method of claim 16, wherein the predicting compensates for a time lag between detection and adjustment, the detection being a detection of a change in the position of the internal region and the adjustment being an adjustment of a treatment beam toward a predicted position of the target region.

22. The method of claim 1, further comprising:
determining the location of the external marker during the treatment; and
determining the position of the target region based on the correlation in response to determining the location of the external marker.

23. The method of claim 1, further comprising:
acquiring another ultrasound image during the treatment; and
updating the correlation based on the other ultrasound image.

24. The method of claim 1, further comprising generating a general model to describe a movement of an anatomic region, wherein the movement of the anatomic region is similar among a plurality of patients.

25. An apparatus for compensating for a motion of an internal target region in a patient during treatment, the apparatus comprising:
a beaming apparatus to generate a treatment beam;
an ultrasound imaging device for periodically generating internal positional data about the internal target region during treatment; and
a processor to receive the internal positional data and external positional data to generate a correlation between a position of the internal target region as determined from the internal positional data and an external marker, wherein the processor is configured to generate a control signal to move the beaming apparatus to direct the treatment beam toward the target region based on the external positional data.

26. The apparatus of claim 25, further comprising an ultrasound guidance system for positioning the ultrasound imaging device to show the target region in an ultrasound image, wherein the ultrasound guidance system includes a remotely operated robotic arm that is connected to the ultrasound imaging device.

27. The apparatus of claim 25, wherein the processor is configured to use the internal positional data, the external positional data, and respiratory data to compensate for movements of the patient.

28. The apparatus of claim 25, wherein the beaming apparatus comprises a multileaf collimator having individual leaves, wherein the beaming apparatus is configured to dynamically move the individual leaves of the multileaf collimator according to the correlation.

29. The apparatus of claim 25, wherein the beaming apparatus is configured to turn the treatment beam on and off.

30. The apparatus of claim 25, further comprising a gantry, wherein the beaming apparatus is mounted on the gantry.

31. The apparatus of claim 25, further comprising a robotic arm, wherein the beaming apparatus is mounted on the robotic arm.

32. The apparatus of claim 31, wherein the robotic arm is configured to move in at least four degrees of freedom.

33. A method for compensating for motions of a patient during treatment, the method comprising:

generating images of a target region prior to the treatment;

periodically generating ultrasound images indicating positional data about the target region during the treatment; and moving a linear accelerator to direct a treatment beam at a position of the target region based on the ultrasound images periodically generated during the treatment.

* * * * *